United States Patent [19]

Sanghvi et al.

[11] Patent Number: 5,117,832
[45] Date of Patent: Jun. 2, 1992

[54] CURVED RECTANGULAR/ELLIPTICAL TRANSDUCER

[75] Inventors: Narendra T. Sanghvi, Indianapolis, Ind.; John N. Zink, Milpitas, Calif.

[73] Assignee: Diasonics, Inc., Milpitas, Calif.

[21] Appl. No.: 750,691

[22] Filed: Aug. 20, 1991

Related U.S. Application Data

[63] Continuation of Ser. No. 585,981, Sep. 21, 1990, abandoned.

[51] Int. Cl.⁵ ............................................. A61B 8/14
[52] U.S. Cl. .......................... 128/662.03; 310/313 R; 310/313 A; 310/367
[58] Field of Search ............ 128/662.03, 662.06, 128/663.01, 660.1, 24 A, 660.03; 310/313 R, 313 A, 313 C, 367; 381/156; 343/831, 832

[56] References Cited

U.S. PATENT DOCUMENTS

| | | | |
|---|---|---|---|
| 2,231,483 | 2/1941 | Smalts | 310/367 |
| 2,468,301 | 4/1949 | Mason | 310/367 |
| 2,567,757 | 2/1947 | Argento | 343/831 |
| 4,248,090 | 2/1981 | Glenn | 128/660.1 |
| 4,601,539 | 7/1986 | Watanabe | 310/369 |
| 4,718,517 | 1/1988 | Carlson | 381/156 |
| 4,762,002 | 8/1988 | Adams | 128/660.1 |
| 4,955,365 | 9/1990 | Fry et al. | 128/660.03 |

Primary Examiner—Francis Jaworski
Assistant Examiner—George Manuel
Attorney, Agent, or Firm—Blakely, Sokoloff, Taylor & Zafman

[57] ABSTRACT

An ultrasound transducer for use in an ultrasound visualization and therapy system or the like. The ultrasound transducer is characterized as a single crystal transducer having a radiating surface which conforms generally in shape to a segment of a surface of a solid of revolution of a conic section, the radiating surface having first and second edges which are generally parallel.

14 Claims, 3 Drawing Sheets

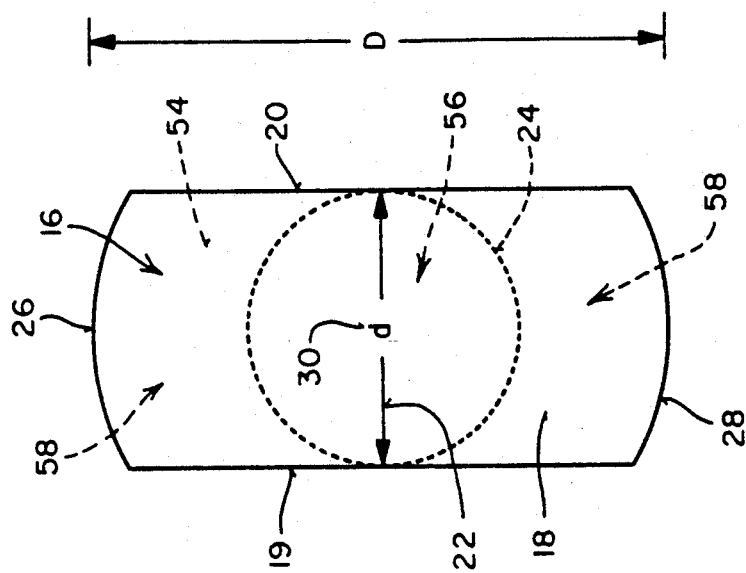
FIG_3
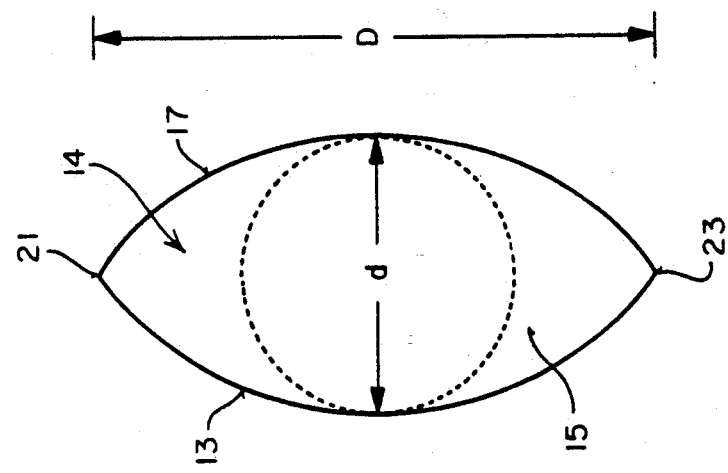
FIG_2
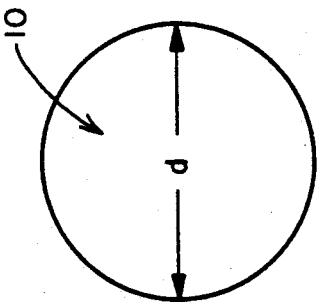
FIG_1

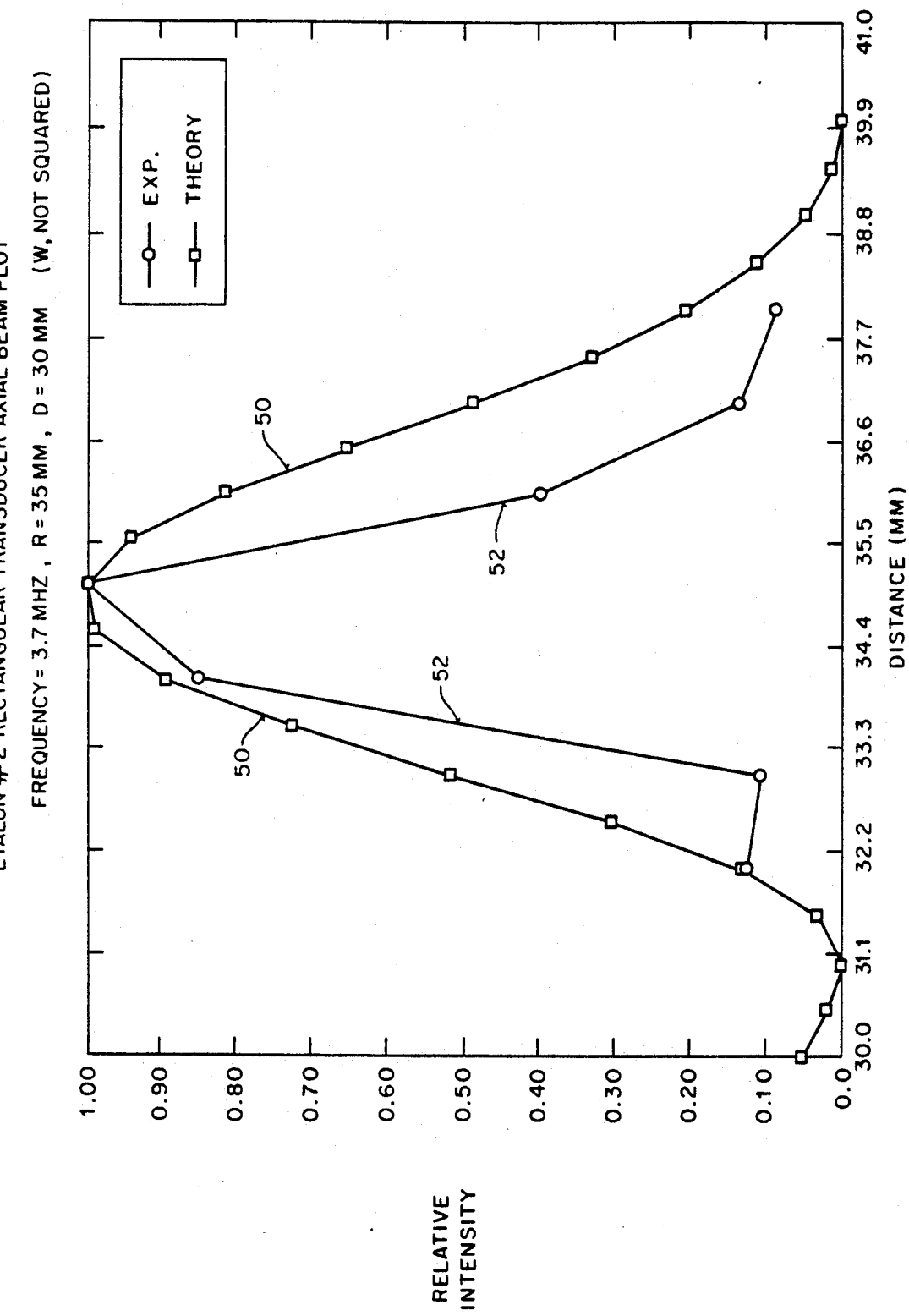
FIG—6

CURVED RECTANGULAR/ELLIPTICAL TRANSDUCER

This is a continuation of application Ser. No. 07/585,981, filed Sep. 21, 1990 now abandoned.

An ultrasound visualization and therapy system typically employs a smaller, lower power visualization transducer and a larger, higher power therapy transducer. Illustrative are the systems described in U.S. Pat. Nos. 4,484,569 and 4,858,613. Typically the radiating surfaces of both the visualization and therapy transducers are surfaces of revolution of segments of the conic sections, particularly circles and ellipses. The focal points of the transducers are at the foci of the transducers' radiating surfaces, for example, the center of a sphere which defines the surface of revolution of the circle, or a focus of an ellipsoid which defines the surface of revolution of the ellipse.

As a general rule, the total acoustic power output of an ultrasound transducer is a function of the area of the radiating surface of the transducer. There are several organs that are difficult to reach by ultrasound for visualization and therapy. Some such organs can be reached by appropriately shaped probes inserted into body cavities and lumens, but the cavities and lumens pose size and shape restrictions on the probes that make transducer design much more difficult. In order to generate the high power necessary for certain therapies, large radiating surfaces are required. This requirement runs generally counter to the dimensional constraints placed upon ultrasound transducers by the need to pass them into and/or through body lumens and cavities to get them into the regions where they are required for visualization and therapy. An example of a procedure which calls for a relatively high power therapy transducer, but also requires the therapy transducer to be small enough to pass into and/or through a small body cavity or lumen would be hyperthermia or tissue ablation prostate therapy. Practically the only way to get the therapy transducer into an effective orientation with respect to the treatment zone is transrectally. However, the treatment itself practically demands a relatively large radiating area therapy transducer, certainly too large to pass transrectally if the radiating surface is designed as the surface of a segment of a sphere or the surface of a segment of an ellipsoid of revolution.

Segmented ultrasound transducers, the shapes of the radiating surfaces of the segments of which are rectangular, are known. See, for example, Hassler et al. U.S. Pat. No. 4,526,168. See also Dory U.S. Pat. No. 4,658,828.

It is an object of the present invention to provide an alternative radiating surface shape for an ultrasound visualization and/or therapy transducer. The alternative shape provides the relatively larger radiating surface area necessary to transmit the higher powers needed for ultrasound hyperthermia, tissue ablation and like therapies. At the same time, this alternative shape accommodates the transducer in a conveniently sized probe for passage into and/or through body cavities and lumens to permit it to be located effectively to the organ or region of the body requiring such therapy.

According to the invention, a transducer has a radiating surface which conforms generally in shape to a segment of a surface of a solid of revolution of a conic section. According to one aspect of the invention, the transducer has first and second edges whose projections onto a plane are generally straight lines.

Illustratively according to this aspect of the invention, the conic section is an ellipse. In the illustrated embodiment, the conic section is a degenerate ellipse, that is, a circle.

Illustratively according to this aspect of the invention, the first and second edges are generally parallel to each other. The first and second edges are equidistantly spaced from a radius of the sphere which defines the radiating surface. The transducer further comprises third and fourth edges which extend between the first and second edges at opposite ends thereof. The third and fourth edges projected into the plane lie generally on arcs of a second circle whose center lies on the radius.

According to another aspect of the invention, a transducer has an edge whose projection onto a plane is somewhat non-degenerately elliptical.

Illustratively according to this aspect of the invention, the projection onto the plane is the projection of two arcs which intersect each other at two points along the major axis of the somewhat elliptical projection.

Additionally according to this aspect of the invention, the two arcs are arcs of circles having diameters substantially greater than the length of the minor axis of the somewhat elliptical projection. Illustratively the circles have diameters greater than twice, and, in an illustrative embodiment, greater than 2.5 times, the length of the minor axis of the somewhat elliptical projection.

Again, illustratively the conic section is an ellipse. In the illustrated embodiment, the conic section is a degenerate ellipse, that is, a circle.

According to either of the illustrated embodiments, the transducer comprises multiple electrodes on the side thereof opposite the radiating surface. One of the multiple electrodes has a circular projection onto the plane.

The invention may best be understood by referring to the following description and accompanying drawings which illustrate the invention. In the drawings:

FIG. 1 illustrates a front elevational view of a circular section, spherical radiating surface ultrasound transducer;

FIG. 2 illustrates a front elevational view of a somewhat elliptical section, spherical radiating surface ultrasound transducer;

FIG. 3 illustrates a front elevational view of a somewhat rectangular section, spherical radiating surface ultrasound transducer;

Figure 5:
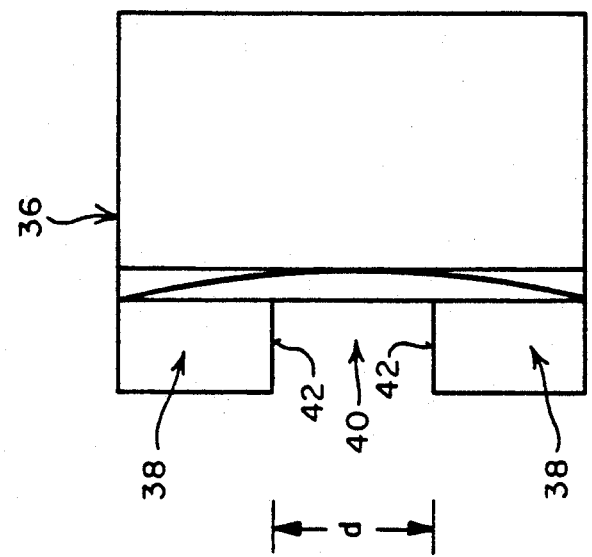
FIG. 5 illustrates a sectional view of the transducer illustrated in FIG. 4, taken generally along section lines 5-5 thereof; and, FIG. 6 illustrates normalized theoretical and experimental ultrasound beam intensities at various distances from the radiating surface of the transducer of FIG. 3, measured along its axis of symmetry.

Referring to FIG. 1, a 12 mm diameter, circular section, spherical radiating surface ultrasound transducer 10 has been demonstrated to be capable of producing a focal lesion on a prostate gland when the transducer 10 is passed transrectally into close proximity to the prostate. However, the lesion is quite small and may be totally ineffective in certain applications, such as the above-noted prostate hyperthermia or tissue ablation treatment.

Referring to FIG. 2, a generally elliptical section, 12 mm minor axis-dimensioned spherical radiating surface ultrasound transducer 14 is illustrated. Transducer 14 is capable of being passed into or through the same body orifice or lumen, and does provide a substantial increase in surface area, and thus radiated power, over the transducer 10 of FIG. 1. The transducer 14 is provided with a part spherical radiating surface 15 and two edges 13, 17 whose projections onto the plane of FIG. 2 are arcs of circles whose diameters are about two and two thirds the diameter d of the circular projection of the transducer 10 in FIG. 1. These edges 13, 17 meet at points 21, 23 which can be thought of as the vertices of the somewhat elliptical projection of transducer 14 onto the plane of FIG. 2. This renders the projection slightly more in the shape of a longitudinal section through a football than a true ellipse, but the term "somewhat elliptical", as used herein, is intended to describe this shape. Of course, transducer 14 can be constructed with a more elliptical, or even exactly elliptical, projection onto the plane of FIG. 2. However, the more elliptical or exactly elliptical configurations are somewhat more difficult to manufacture than the somewhat elliptical configuration illustrated in FIG. 2, and the performance benefits of the more elliptical or exactly elliptical projection transducers are believed to be only marginally better than the performance of the somewhat elliptical one illustrated in FIG. 2. However, even a transducer having the somewhat elliptical sectional configuration of transducer 14 is rather difficult to manufacture.

Referring to FIG. 3, the problems of radiated power capability, a shape which permits passage into/through smaller body orifices and/or lumens, and ease and simplicity of manufacture are all effectively addressed by a transducer 16 with a radiating surface 18 which has the same spherical curvature as the circular section transducer 10 of FIG. 1 and the generally elliptical section transducer 14 of FIG. 2, but has two long parallel edges 19, 20 which, when viewed in elevation, appear to extend along tangents to a diameter 22 of an inscribed circle 24 of the same diameter, d, as the transducer 10 of FIG. 1. The short edges 26, 28 of the transducer 16 radiating surface 18 which extend between the parallel edges 19, 20 thereof are arcs of a circle of diameter D whose center 30 lies at the geometric center of the section 16. Thus, the elevational projection of the section 16 is not precisely rectangular, but rather, is the region of a circle of diameter D bounded by two chords 19, 20 of that circle which are parallel and equidistant (at d/2 units) from its center 30. However, this transducer section 16 may be thought of as generally rectangular, since the diameter D of that circle is rather larger than the diameter of the inscribed circle 24 which is the same size as section 10 of FIG. 1.

It will be immediately appreciated that the area of the radiating surface 18 of the transducer 16 of FIG. 3 is not only more than twice as large as the radiating surface area $\pi d^2/4$ of the transducer 10 of FIG. 1, but it is also considerably larger than the radiating surface area of the transducer of FIG. 2. At the same time, the transducer 16 of FIG. 3 is capable of being passed into and/or through the same body orifices or lumens as the smaller radiating surface area transducers 10 and 14 of FIGS. 1-2. In addition, the shape illustrated in FIG. 3 immediately suggests a manufacturing technique which renders the transducer 16 of FIG. 3 somewhat simpler to fabricate than the transducer 14 of FIG. 2. Further, the shape illustrated in FIG. 3 also immediately suggests a concept testing technique for determining the size of transducer 16 required to transmit a particular power at a particular frequency to provide the requirements of a particular application.

The construction techniques for transducers of the type described in FIG. 1 are well known. Indeed these are the types of transducers employed in the systems of the above-identified patents. In order to manufacture a transducer 16 of the type illustrated in FIG. 3, it is only necessary to manufacture one of the type illustrated in FIG. 1, but with the much longer diameter D than the diameter d of the transducer illustrated in FIG. 1. Then the transducer is cut along two parallel chords 19, 20 of its elevational projection. These chords are d/2 units from its geometric center 30. This yields the generally rectangular section transducer 16 of FIG. 3.

Figure 4:
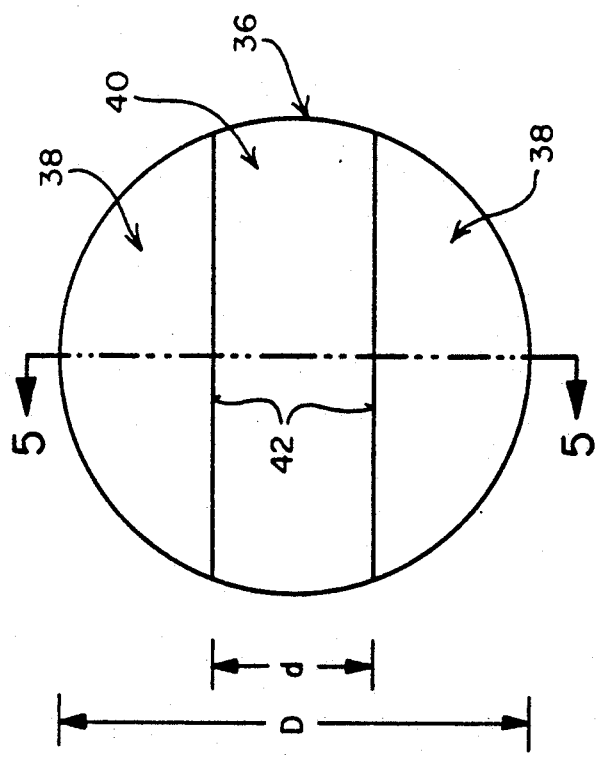
FIG. 4 illustrates a front elevational view of a circular section, spherical radiating surface ultrasound transducer prepared to demonstrate the concept of the present invention.

As noted above, this also suggests a technique for testing to determine the size of transducer 16 adequate for performing a particular therapy. That technique is best illustrated in FIGS. 4-5. In that technique, a circular elevation transducer 36 of diameter D is masked by two somewhat D-shaped ultrasound energy absorbing elements 38. This leaves exposed in front elevation only the somewhat rectangular region 40 between the adjacent parallel faces 42 of elements 38. This region 40 has width d. The transducer 36 thus masked can be tested on conventional ultrasound test equipment to determine the power output of region 40 at any ultrasound frequency of interest.

The rather dramatic increase in intensity which is available with the transducer 16 of FIG. 3 over transducers of the type illustrated in FIG. 1 does, however, give rise to a minor problem. That problem is one of visualization. The ultrasound diagnostician is used to viewing ultrasound echo-derived images which return from an ultrasound field having a particular lower visualization intensity. The high ultrasound field intensity available with the invention of FIG. 3 is normalized and compared to the theoretical, somewhat Gaussian ultrasound field intensity in FIG. 6. The theoretical field intensity is plotted at 50. The normalized experimental ultrasound field intensity available with the transducer 16 of FIG. 3 is plotted at 52. As is apparent from these curves, the field intensity available with the transducer 16 of FIG. 3 is considerably "peakier" directly in front of (along the axis of symmetry of) the transducer 16. As a result, the ultrasound echo-derived image which the diagnostician observes is rather more intense in the region of this peak than he or she is used to viewing in making a diagnosis. In order to avoid the errors in diagnosis which might otherwise result from using the entire transducer 16 to generate the visualization field, the back electrode 54 of the transducer 16 is separated, for example, by scoring at 24, into a central circular region 56 of the same configuration as transducer 10 of FIG. 1 and two "wings" 58. When transducer 16 is being used for visualization, region 56 can be activated alone. This produces the conventional image which the diagnostician is used to seeing and interpreting, without the need for complex phasing or amplitude adjustment electronics in the visualization electronics. Then, when treatment is being conducted, the back electrode metallizations of all three regions 56, 58 are energized simultaneously. This provides the higher power previously described at the focal region for hyperthermia, tissue ablation therapy, and like therapies.

What is claimed is:

1. An ultrasound single crystal transducer having a radiating surface which conforms generally in shape to a segment of a surface of a solid of revolution of a conic section, said radiation surface having first and second edges.

2. The transducer of claim 1 wherein the conic section is an ellipse.

3. The transducer of claim 2 wherein the ellipse is a circle and the solid of revolution is thereby a sphere.

4. The transducer of claim 3 wherein the first and second edges are equidistantly spaced from a radius of the sphere which defines the radiating surface.

5. The transducer of claim 4 wherein the transducer further comprises third and fourth edges which extend between the first and second edges at opposite ends thereof.

6. The transducer of claim 5 wherein the third and fourth edges projected into the plane lie generally on arcs of a second circle whose center lies on the radius of the sphere.

7. The transducer of one of claims 1 through 3 and 4 through 6 further comprising multiple electrodes on the side thereof opposite the radiating surface, one of the multiple electrodes having a generally circular projection onto the plane.

8. An ultrasound single crystal transducer having a radiating surface which conforms generally in shape to a segment of a surface of revolution of a conic section, said crystal further having a side opposite said radiating surface, and said crystal further having an edge which defines an ellipse having a major axis longer than its minor axis.

9. The transducer of claim 8 wherein the two arcs are arcs of circles having diameters substantially greater than the length of the minor axis of the ellipse.

10. The transducer of claim 9 wherein the two arcs are arcs of circles having diameters greater than about twice the length of the minor axis of the ellipse.

11. The transducer of claim 10 wherein the two arcs are arcs of circles having diameters greater than about 2.5 times the length of the minor axis of the ellipse.

12. The transducer of claim 11 wherein the conic section is an ellipse.

13. The transducer of claim 12 wherein the ellipse is a circle.

14. The transducer of one of claims 8 through 15 further comprising multiple electrodes on the side thereof opposite the radiating surface, one of the multiple electrodes having a generally circular projection onto the plane.

* * * * *

UNITED STATES PATENT AND TRADEMARK OFFICE
CERTIFICATE OF CORRECTION

PATENT NO. : 5,117,832

DATED : 6/2/92

INVENTOR(S) : Narendra T. Sanghvi & John N. Zink

It is certified that error appears in the above-indentified patent and that said Letters Patent is hereby corrected as shown below:

Column 5, line 6, after the word "edges"  Insert--which are generally parallel.

Signed and Sealed this

Twenty-fourth Day of August, 1993

Attest:

BRUCE LEHMAN

Attesting Officer

Commissioner of Patents and Trademarks